(12) United States Patent
De Lavigne Sainte Suzanne

(10) Patent No.: US 9,987,065 B2
(45) Date of Patent: Jun. 5, 2018

(54) INTRAOSSEOUS SCREW FOR FIXING A BONE FRAGMENT OR A TRANSPLANT TO A BONE AND METHOD FOR MANUFACTURING SUCH AN INTRAOSSEOUS SCREW

(71) Applicant: Christophe De Lavigne Sainte Suzanne, Bordeaux (FR)

(72) Inventor: Christophe De Lavigne Sainte Suzanne, Bordeaux (FR)

( * ) Notice: Subject to any disclaimer, the term of this patent is extended or adjusted under 35 U.S.C. 154(b) by 426 days.

(21) Appl. No.: 14/440,691

(22) PCT Filed: Oct. 31, 2013

(86) PCT No.: PCT/FR2013/052616
§ 371 (c)(1),
(2) Date: May 5, 2015

(87) PCT Pub. No.: WO2014/068259
PCT Pub. Date: May 8, 2014

(65) Prior Publication Data
US 2015/0250513 A1    Sep. 10, 2015

(30) Foreign Application Priority Data
Nov. 5, 2012 (FR) ...................... 12 60471

(51) Int. Cl.
*A61B 17/86* (2006.01)
*A61B 17/00* (2006.01)

(52) U.S. Cl.
CPC .......... *A61B 17/869* (2013.01); *A61B 17/864* (2013.01); *A61B 17/866* (2013.01); *A61B 17/8645* (2013.01); *A61B 2017/00526* (2013.01)

(58) Field of Classification Search
CPC .. A61B 17/869; A61B 17/864; A61B 17/8645
See application file for complete search history.

(56) References Cited

U.S. PATENT DOCUMENTS

| | | | | |
|---|---|---|---|---|
| 6,056,749 A | * | 5/2000 | Kuslich | A61B 17/025 606/247 |
| 7,736,381 B2 | * | 6/2010 | Biedermann | A61B 17/864 606/301 |

(Continued)

FOREIGN PATENT DOCUMENTS

| | | |
|---|---|---|
| WO | 96/40020 A1 | 12/1996 |
| WO | 2008/021474 A2 | 2/2008 |
| WO | 2008/092192 A1 | 8/2008 |

OTHER PUBLICATIONS

Jan. 14, 2014 Search Report issued in International Patent Application No. PCT/FR2013/052616.

(Continued)

*Primary Examiner* — Christian Sevilla
(74) *Attorney, Agent, or Firm* — Oliff PLC

(57) ABSTRACT

An intraosseous screw includes at least one external thread, a receiving element extending into and parallel to the external thread, and connecting members connecting the individual screw threads of the external thread. The or each external thread has capillary through-channels that pass through the screw so as to end in the receiving element. The connecting members define a plurality of through-openings. The receiving element is shaped so as to be able to receive a cylindrical bone portion once the intraosseous screw has been screwed into the bone.

18 Claims, 3 Drawing Sheets

(56) References Cited

U.S. PATENT DOCUMENTS

2004/0015172 A1     1/2004   Biedermann et al.
2009/0319043 A1    12/2009   McDevitt et al.

OTHER PUBLICATIONS

May 5, 2015 International Preliminary Report on Patentability issued in International Patent Application No. PCT/FR2013/052616.

* cited by examiner

INTRAOSSEOUS SCREW FOR FIXING A BONE FRAGMENT OR A TRANSPLANT TO A BONE AND METHOD FOR MANUFACTURING SUCH AN INTRAOSSEOUS SCREW

The present invention relates to an intraosseous screw to be implanted in a bone. In addition, the present invention relates to a method for manufacturing such intraosseous screw.

The present invention can be applied in any medical field where it is necessary to implant an intraosseous screw into a bone. Furthermore, the present invention can be applied in osteosynthesis for fixing a bone fragment to a bone, generally to repair a fracture. The present invention can also be applied in ligament surgery for fixing a transplant to a bone, by passing this transplant through a bone tunnel.

In the background art, to place an osteosynthesis or interference screw, one should use a bit or a drill, in order to prepare a tunnel to make the head and web of the screw penetrate in the middle of the drilled pilot hole. Some resorbable screws are molded by polylactic acid injection (PLA) to a mixture of polylactic acid (PLA) and hydroxyapatite or a mixture of polylactic acid (PLA) and tricalcium phosphate.

However, these screws in resorbable materials molded by injection are not permeable enough to the liquid medium to allow a rapid absorption, that is to say, within the given period for good bone integration.

In addition, there are known intraosseous screws having a housing for receiving pieces of crushed bone or an insert for fixing a ligament. This type of intraosseous screw of the background art has solid walls for the mechanical strength of the intraosseous screw. These solid walls result from molding and are hence essentially waterproof. Such an intraosseous screw sometimes has a few localized windows in order to lighten the intraosseous screw. Furthermore, a screw of the background art has a screw head for perforating the bone.

However, such an intraosseous screw causes trauma to the bone, as it requires cutting a portion of bone, thus, decreasing the bone mass. In addition, since their walls are solid, the bone reconstruction cannot take place in the opening where the intraosseous screw is housed. Hence, such an intraosseous screw does not allow or hardly allows the reconstruction of the bone tissue in the housing.

The aim of the present invention is in particular to solve, all or part of the aforementioned issues.

To this end, the invention relates to an intraosseous screw, intended for fixing a bone fragment to a bone for an osteosynthesis or a transplant for a ligament surgery, the intraosseous screw comprising:
 at least one outer threading, which is formed by a plurality of threads and which extends along a so-called helix around a longitudinal axis;
 a housing which extends inside the outer threading and generally parallel to the longitudinal axis;
 connecting members arranged in such a manner as to connect the threads together;
 the intraosseous screw being characterized in that the connecting member comprise spacers, each spacer preferably connecting at least two consecutive threads, the spacers being arranged in such a manner as to define a multitude of through openings which open into the housing,
 and in that the housing delimits a hollow cylindrical volume which opens into at least one end of the outer threading, the hollow cylindrical volume being shaped in such a manner as to house, after screwing of the intraosseous screw into the bone, a cylindrical portion of bone.

This cylindrical portion of bone most often originates from the bone of the patient. Thus, such an intraosseous screw may be screwed into a bone via the outer threading. In addition, osteoblasts may settle in the housing and through the many through openings, thus, allowing a rapid bone reconstruction in and around the intraosseous screw.

The connecting members support the outer threading, thus imparting mechanical strength to the intraosseous screw. Each through opening is defined by spacers and, in most cases, also by threads of the outer threading. The spacers allow arranging relatively large through openings, while imparting high mechanical resistance to the outer threading, hence to the intraosseous screw. Typically, the multitude of through openings may include several dozens, or even several hundreds of through openings delimited by the spacers.

In some operations (ligament surgery with intraosseous screw called interference screw), a bone core can be inserted into the housing. The through openings allow the blood to flow towards and out of the housing, in such a manner as to irrigate the bone core.

Alternatively, in the case of an osteosynthesis, for the bone repair, an intraosseous screw in accordance with the invention may be screwed into the bone, after a possible preparation of the bone by a trephine, thus isolating a portion of bone in the housing of the intraosseous screw. In this alternative, one does not hollow out a bore with total bone loss at the site occupied by the drill. On the contrary, the trephine does not remove the initial bone of the patient and only scoops out a minimum volume which is to be occupied by the intraosseous screw. After screwing the intraosseous screw, the through openings allow blood to flow towards and out of the housing, in such a manner as to irrigate this portion of bone which has been isolated from the bone of the patient, but not removed from the bone of the patient.

In a manner known per se, the intraosseous screw can be inserted using a screwdriver. The cap of the intraosseous screw can be achieved according to any existing model for any type of screwdriver, particularly in the case of an intraosseous screw for osteosynthesis, which does not require reintroducing the bone core from the back of intraosseous screw.

According to a variant of the invention, the threads form a continuous outer threading. In other words, these threads are intact, therefore not sectioned. Thus, such an outer threading has a high mechanical strength.

According to a variant of the invention, the intraosseous screw comprises at least two outer threadings which are wound along two parallel helices and of different pitches around the longitudinal axis. Thus, such outer threadings can absorb important mechanical forces of compression type of an area of fracture.

According to a variant of the invention, the connecting members form a cylindrical core coaxial with the longitudinal axis, said at least one outer threading extending around the core. Thus, the intraosseous screw may be manufactured by securing, for example by bonding, the core to the outer threading.

According to a variant of the invention, said at least one outer threading being composed of at least one biocompatible and bioresorbable material. Thus, the intraosseous screw can be partially or completely resorbed. According to one embodiment of the invention, the transverse dimensions of the housing are greater than 90% of the minimum dimension of the inner part of the outer threading.

Thus, the housing may house a cylindrical portion of bone of relatively large diameter, thus preserving the bone mass and providing a high mechanical strength to this portion of bone.

According to one embodiment of the invention, the hollow cylindrical volume opens at the two ends of the outer threading, in such a manner that, after screwing the intraosseous screw into the bone, the outer threading can house a portion of bone remaining secured to the bone.

In other words, the intraosseous screw is devoid of screw head, at least at one end of the intraosseous screw. Thus, such an intraosseous screw (interference screw for osteosynthesis) can be tightened in the bone without prior removal of a bone core, thus minimizing the bone loss of the patient.

According to one embodiment of the invention, the hollow cylindrical volume of housing has a diameter substantially equal to the inner diameter of the end portion of the outer threading.

Thus, the housing may house a cylindrical portion of bone of large diameter, thus preserving the bone mass.

According to one embodiment of the invention, the spacers intersect at least in pairs.

In other words, two neighboring spacers form an intersection. Thus, such crossings or intersections increase the mechanical strength of the intraosseous screw.

According to one embodiment of the invention, the spacers comprise:
- so-called opposite spacers which generally extend along so-called opposite helices which are oriented inversely to the external helix of said at least one outer threading; and
- so-called direct spacers which generally extend along so-called direct helices which are oriented like the external helix of said at least one outer threading.

In other words, when the outer threading follows an external helix which is dextral (pitch on the right), the opposite spacers follow opposite helices which are sinistral (pitch on the left). When the outer threading follows an external helix which is dextral (pitch on the right), the direct spacers follow direct helices which are dextral (pitch on the right).

Thus, the presence of direct spacers and opposite spacers achieves a cross meshing such as a mesh fence, thus imparting the intraosseous screw with a mechanical strength to all the efforts it has to bear. Particularly, opposite spacers resist efforts, in particular, in torsion around the longitudinal axis, to which the outer threading has little resistance.

According to a variant of the invention, the intraosseous screw has nodes between two consecutive threads, each node being formed by the intersection of at least two spacers.

Thus, such nodes or braces increase the mechanical strength of the intraosseous screw.

According to one embodiment of the invention, said at least one outer threading has a plurality of so-called capillary channels which cross said at least one outer threading in such a manner as to open into the housing.

Thus, such capillary channels largely contribute to the circulation of blood to and outside the housing, hence to the bone reconstruction in the housing and to the resorption of the intraosseous screw.

According to one embodiment of the invention, spacers, preferably the majority of the spacers, have through capillary channels in such a manner as to open into the housing.

Thus, such capillary channels largely contribute to the circulation of blood to and outside the housing, hence to the bone reconstruction in the housing and to the resorption of the intraosseous screw.

In the present application, the term "capillary channel" refers to a channel which allows the flow of blood by capillarity. The dimensions of a capillary channel are such that a pumping effect occurs between the ends thereof. This observed pumping effect is caused by capillarity, due to the capillaries resulting from a meshing of fibers, by Venturi effect, by gas exchanges between the bone of the patient and the cylindrical portion placed in the hollow cylindrical housing.

According to a variant of the invention, the capillary channels are regularly distributed, preferably uniformly, on the outer threading. Thus, this uniform distribution of capillary channels in particular promotes bone reconstruction.

According to one embodiment of the invention, capillary channels and/or through openings have shapes converging from an outer surface of the outer threading towards the housing, and capillary channels and/or through openings have shapes diverging from an outer surface of the outer threading towards the housing.

Thus, such converging and diverging shapes promote the flow of blood by capillarity through these capillary channels and these through openings. The converging channels promote the entry of the liquid into the housing, whereas the diverging channels promote the exit of the liquid from the housing.

According to a variant of the invention, capillary channels, preferably all the capillary channels, have transverse dimensions lower than 1.5 mm, preferably lower than 1 mm.

Thus, such transverse dimensions allow a good circulation of the blood by capillarity through the capillary channels and/or the through openings.

According to one embodiment of the invention, said at least one outer threading and the connecting members are respectively composed of compressed fibers.

Thus, in addition to the capillary channels and through openings which are relatively wide and where the blood flows rapidly, the intraosseous screw has secondary capillaries, which extend along compressed fibers and which are narrower. The blood flows more slowly through these secondary capillaries than through the capillary channels and through openings, but the blood can cross a greater distance therein. In addition, such compressed fibers make the intraosseous screw both mechanically strong and relatively light.

Such an intraosseous screw may be manufactured out of resorbable fibers by centrifugal spinning, preferably called "rotary jet spinning" or by electrostatic spinning called "electrospinning", wherein a fluid is projected according to a rotary movement in such a manner as to agglomerate fibers which are oriented and positioned by means of an electrostatic field.

According to one embodiment of the invention, the compressed fibers comprise fibers composed of lactic acid polymer (PLA), and as the case may be bioresorbable fibers which are preferably composed of materials selected from among the group consisting of collagen, hydroxyapatite and caprolactone.

Thus, such fibers are biocompatible and can be compressed by various methods, for example electrospinning or rotary jet spinning, or by rotational molding, or even woven and then wound around an axis.

According to one embodiment of the invention, the compressed fibers further comprise fibers of strontium.

Thus, the fibers of strontium make the intraosseous screw radiopaque, thus facilitating the medical imaging by X-ray radiography or with an image intensifier.

According to a variant of the invention, all or part of the compressed fibers may be covered with spheroidal particles made of a bioactive ceramic-glass material, the spheroidal particles preferably having a dimension lower than 2 µm, preferably lower than 1 µm.

Thus, such spheroidal particles facilitate bone adhesion. Such a bioactive ceramic-glass material is commercialized for example as "bioglass".

According to one embodiment of the invention, the intraosseous screw further comprises a screw head arranged in such a manner that the intraosseous screw can be tightened in a bore after previous removal of a portion of a generally cylindrical bone.

Thus, such an intraosseous screw fulfills the function of interference screw and allows fixing a transplant to a bone, for example for a ligament surgery. The generally cylindrical portion of bone may then be reinserted into the housing.

According to a variant of the invention, each thread has a thickness between 0.5 mm and 1.5 mm, preferably between 0.8 mm and 1.2 mm.

Thus, such an outer threading may be suited to various operations. The dimensions of the outer threading allow a quick and lasting implantation of the intraosseous screw and minimization of the size of the hole to be bored into the bone by means of a trephine, hence bone loss in the case of osteosynthesis.

According to a variant of the invention, each thread has a thread crest or a thread head the profile of which is rounded. Thus, such a rounded profile prevents the thread head from locally cutting a tendinous tissue or artificial interference tissue.

According to a variant of the invention, each thread has a profile with a generally "Y" shape, the tail of the "Y" forming the head of the respective thread.

Thus, such a "Y" profile allows minimizing the thickness of the outer threading to resorbed and maximizing the size of the housing in which the tissue will grow.

According to one embodiment of the invention, the intraosseous screw further comprises a so-called inner threading which extends on the edges of the housing.

Thus, such an inner threading allows screwing an insert to fix a transplant with the intraosseous screw, hence to a bone, for a ligament surgery.

According to a first variant of this embodiment of the invention, the intraosseous screw comprises an inner threading substantially extending over the entire length of the intraosseous screw, in such a manner as to increase its stability on the bone (osteoporosis). In a second variant of this embodiment of the invention, the intraosseous screw comprises an inner threading extending only over a posterior part of the intraosseous screw, in such a manner as to fix a transplant with the intraosseous screw.

Advantageously, the inner threading extends only over a posterior portion of the intraosseous screw.

According to a variant of the invention, the intraosseous screw further comprises an eyelet or equivalent secured to a posterior end of the intraosseous screw. Thus, such an eyelet allows forming a headless, hollow anchor, the eyelet serving to pass a double anchoring wire inserted in the back of the screw, in order to fix ligament attachments.

According to a variant of the invention, the outer threading has a length between 1 mm and 10 mm, preferably between 1 mm and 5 mm.

According to one embodiment of the invention, the spacers are formed by rods, preferably of a generally circular section.

According to one embodiment of the invention, each spacer extends between two consecutive threads. In other words, each spacer is delimited by two consecutive threads. Put another way, each spacer has a first end disposed on a thread and a second end disposed on the consecutive thread.

Thus, the spacers and the outer threading are distinct pieces, thus simplifying the production of the intra-osseous screw, particularly of small dimensions, and imparting a high mechanical strength to the outer threading.

According to one embodiment of the invention, the spacers are configured in such a manner that the combined surface area of the through openings represents at least 50%, preferably at least 70% of the surface delimited between the threads.

In other words, most of this surface is open. This surface has a generally helical shape. Thus, such an intraosseous screw largely promotes bone growth through the intraosseous screw.

According to one embodiment of the invention, the intraosseous screw comprises at least 5 spacers, preferably at least 8 spacers, between two consecutive threads.

Furthermore, the present invention relates to a manufacturing method, for manufacturing an intraosseous screw according to the invention, the manufacturing method comprising steps of projecting fibers in a mold the cavity of which defines the intraosseous screw, the projection being preferably carried out by so-called "rotary jet spinning" or by electrostatic spinning under the control of a computer.

Thus, such a manufacturing method allows manufacturing intraosseous screws of small size at a reasonable cost. Alternatively, the projection of the fibers may be carried out by rotary jet spinning or by conventional rotational molding spinning or woven around an axis.

Alternatively to this manufacturing method, it is possible to manufacture an intraosseous screw in accordance with the invention by achieving a generative method, such as selective sintering by a laser.

The aforementioned embodiments and variants may be taken alone or according to any technically possible combination.

The present invention will be well understood and its advantages will also become apparent in light of the following description, given only by way of non limiting example and made with reference to the accompanying drawings, wherein.

FIGS. 1, 2, 3, 4 and 5 illustrate an intraosseous screw 1 without a screw head in accordance with a first embodiment of the invention. The intraosseous screw 1 is intended to fix to a bone a transplant for ligament surgery.

Figure 1:
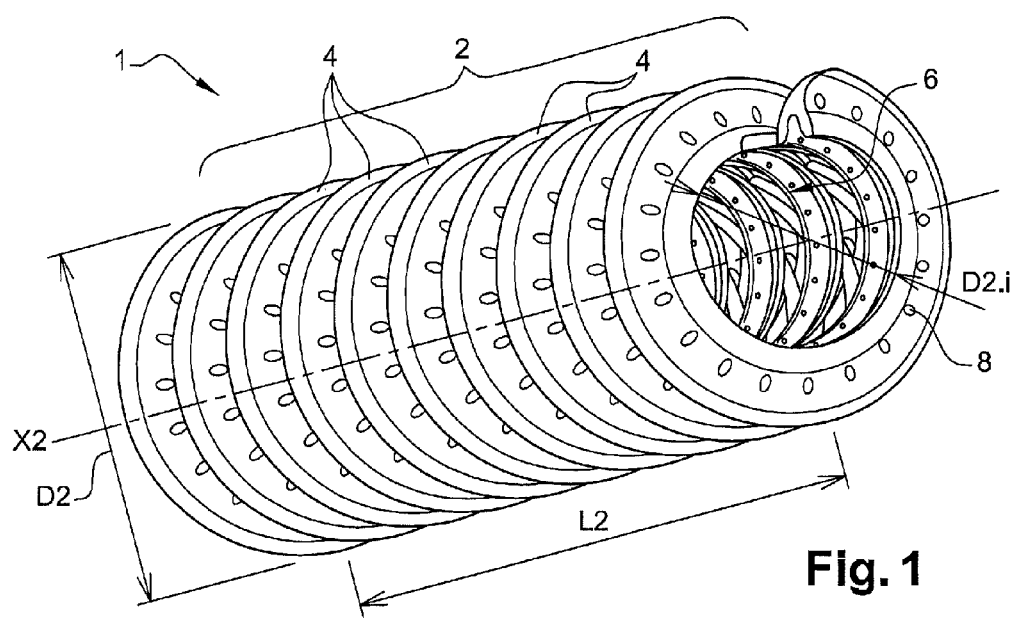
FIG. 1 is a perspective view of an intraosseous screw without a head in accordance with a first embodiment of the invention.
Figure 2:
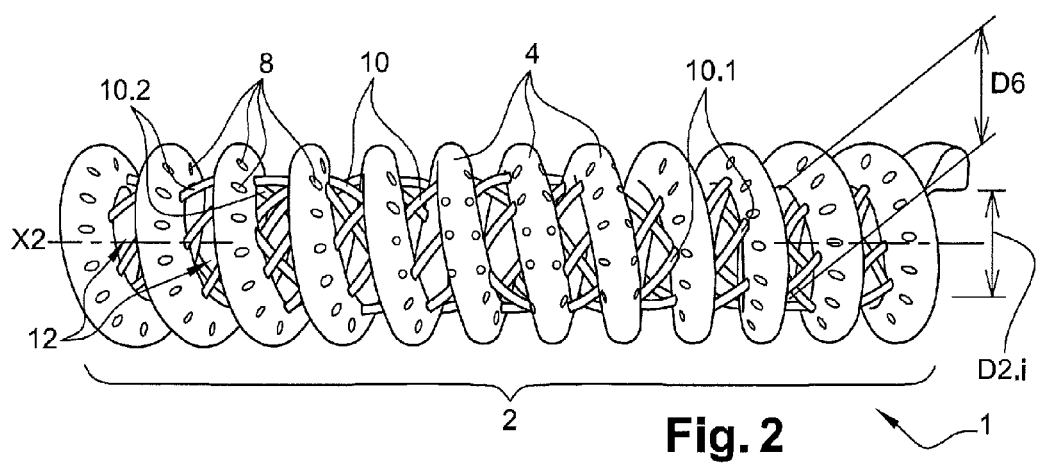
FIG. 2 is a perspective view, according to an angle different from FIG. 1, of the intraosseous screw of FIG. 1.
Figure 3:
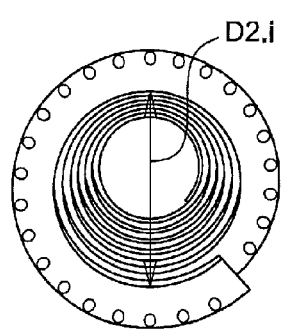
FIG. 3 is a perspective front view of the intraosseous screw of FIG. 1.

The intraosseous screw 1 comprises an outer threading 2 which is formed by a plurality of threads 4. The outer threading 2 extends along a so-called external helix around a longitudinal axis X2. In the example of FIGS. 1 and 2, the threads 4 form an outer threading 2 which is continuous.

Each thread 4 has here a thickness of around 1 mm. The outer threading 2 has here a length L2 of around 4 mm and an outer diameter D2, measured on the crest of the thread 4, around 1 mm. Obviously, the dimensions, length and outer diameter, of an intraosseous screw in accordance with the invention may be adapted to the intended application.

In addition, the intraosseous screw 1 comprises a housing 6 a part of which is visible in FIG. 1. The housing 6 extends inside the outer threading 2 and generally parallel to the longitudinal axis X2.

The housing 6 delimits a hollow cylindrical volume which opens onto the two ends of the outer threading 2 (intraosseous screw 1 without a head). The hollow cylindrical volume is shaped in such a manner that, after screwing of the intraosseous screw 1 into the bone, the hollow cylindrical volume, hence the outer threading 2, may house a bone portion, not represented, which remains secured to the bone and which is substantially cylindrical. This bone portion can originate from the bone of the patient.

Thus, the hollow cylindrical volume of housing 6 is shaped for housing, after screwing of the intraosseous screw 1 into the bone, a cylindrical portion of bone. The transverse dimensions of the housing 6 are greater than 90% of the minimum dimension of the inner part of the outer threading 2. Here, the hollow cylindrical volume of the housing 6 has a diameter D6 which is substantially equal to the inner diameter of the portion D2.i of the end portion of the outer threading 2.

The outer threading 2 has several so-called capillary channels 8 which cross the outer threading 2 in such a manner as to open into the housing 6. In the example of FIGS. 1 to 5, the capillary channels 8 are regularly distributed over the outer threading 2. The capillary channels 8 are here distributed substantially uniformly over the outer threading 2.

The intraosseous screw 1 further comprises spacers 10. As shown in FIG. 2, the intraosseous screw 1 comprises around 10 spacers 10 between two consecutive threads 4. Each spacer 10 here generally has the shape of a rod of a generally circular section.

Each spacer 10 connects two consecutive threads 4. Each spacer 10 extends here between two consecutive threads 4. In other words, each spacer 10 is delimited by two consecutive threads 4. The spacers 10 here form connecting members arranged in such a manner as to connect the threads 4 together. Each spacer 10 connects two consecutive threads 4 together.

The spacers 10, which compose the connecting members, are arranged in such a manner as to define therebetween a multitude of through openings 12 which open into the housing 6. The through openings 12 are here defined by interstices extending between spacers 10. Each through opening 12 is defined by spacers 10 as well as by threads 4 of the outer threading 2. In addition, spacers 10 may also have through capillary channels in such a manner as to open into the housing 6.

In the example of FIGS. 1 and 2, the spacers 10 are configured in such a manner that the combined surface area of the through openings 12 represents around 90% of the surface delimited between the threads 4.

The spacers 10 comprise so-called opposite 10.1 spacers which extend generally along so-called opposite helices which are oriented inversely to the external helix of the outer threading 2. The outer threading 2 runs along an external helix which is dextral (pitch on the right). The opposite helices hence have a pitch on the left.

The spacers 10 further comprise so-called direct 10.2 spacers which extend generally along so-called direct helices which are oriented just as the external helix of the outer threading 2. Direct helices hence have a pitch on the right.

In addition, the intraosseous screw 1 has nodes 14 between two consecutive threads 4. Each node 14 is here formed by the intersection of two spacers 10, usually an opposite spacer 10.1 and a direct spacer 10.2. At least two neighboring spacers 10.1 and 10.2 meet in a node 14.

Furthermore, each thread 4 has a generally "Y" shaped profile, the tail of the "Y" forms the head of the respective thread. Each thread has a thread head the profile of which is rounded. The "Y" profile of the threads 4 is materialized in dotted lines on FIG. 5.

The outer threading 2 and the spacers 10 which form connecting members are respectively composed of compressed fibers F, visible on FIG. 1. These compressed fibers here comprise fibers composed of lactic acid polymer (PLA), collagen fibers and hydroxyapatite fibers.

The compressed fibers further comprise strontium fibers, which make the intraosseous screw 1 radio-opaque. In addition, some of the compressed fibers are covered with spheroidal particles in a bioactive ceramic-glass material, the spheroidal particles preferably having a dimension lower than 2 μm, preferably lower than 1 μm.

Thus, such spheres facilitate the bone adhesion. Such a bioactive ceramic-glass material is commercialized, for example as "bioglass" or reference BaG 13.93. The spheroidal particles may be covered with poly-L, DL lactic acid (for example known under the reference SR-PLA70).

As the capillary channels 8 and the through openings 14 are relatively wide, the blood will flow quickly therein. When composed of compressed fibers, the intraosseous screw 1 has secondary capillaries which are not represented, which extend along compressed fibers and which are narrower. The blood flows more slowly through these secondary capillaries than through the capillary channels 8 and the through openings 14. However, the blood can cross, by capillarity, a greater distance through these secondary capillaries than through the capillary channels 8 and the through openings 14.

Figure 9:
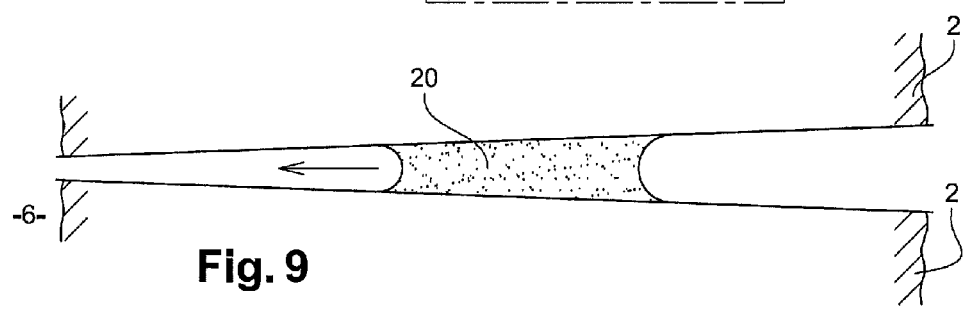
FIG. 9 is a schematic view of a capillary channel formed in an intraosseous screw in accordance with the invention.

Some of the capillary channels 8 have shapes converging from an outer surface of the outer threading 2 towards the housing 6. As shown schematically on FIG. 9, a capillary channel 8 converges from the upstream, located on the side of the outer threading 2, towards the downstream, located on the side of the housing 6, thereby allowing the blood flow by capillarity. Conversely, some of the capillary channels 8 have shapes diverging from an outer surface of the outer threading 2 towards the housing 6.

A regular shift of the compressed fibers allows forming capillary channels 8 the direction of which is towards the housing 6, and capillary channels 8 the direction of which is back, out of the housing 6. When the blood can come to and go out of the housing 6, it circulates all around and in the intraosseous screw 1, thus facilitating the settling of the osteoblasts and the acceleration of the bone reconstruction.

As the capillary channels 8 and through openings 14 are relatively wide, the blood will flow quickly therein. When composed of compressed fibers, the intraosseous screw 1 has secondary capillaries which are not represented, which extend along compressed fibers and which are narrower. The blood flows more slowly through these secondary capillaries than through the capillary channels 8 and the through openings 14. However, the blood may cross, by capillarity, a greater distance through these secondary capillaries than through the capillary channels 8 and the through openings 14.

Some of the capillary channels 8 have shapes converging from an outer surface of the outer threading 2 towards the housing 6. As shown schematically on FIG. 9, a capillary channel 8 converges from the upstream, located on the side of the outer threading 2, towards the downstream, located on the side of the housing 6, thereby allowing the blood flow by capillarity 20. Conversely, some of the capillary channels 8 have shapes diverging from an outer surface of the outer threading 2 towards the housing 6.

A regular shift of the compressed fibers allows forming capillary channels 8 the direction of which is towards the housing 6, and capillary channels 8 the direction of which is back, out of the housing 6. When the blood can come to and go out of the housing 6, it circulates all around and in the intraosseous screw 1, thus facilitating the settling of the osteoblasts and the acceleration of the bone reconstruction.

Figure 6:
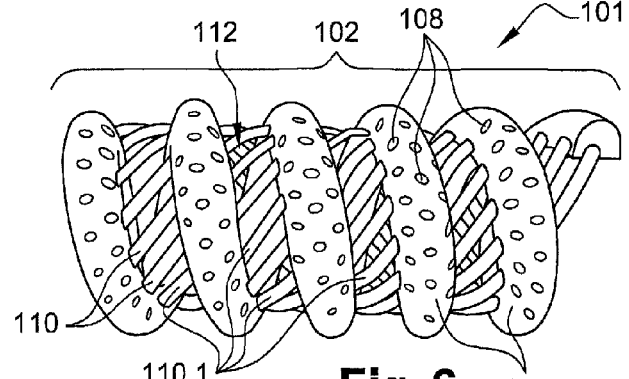
FIG. 6 is a view similar to FIG. 2 of an intraosseous screw without a head in accordance with a second embodiment of the invention.
Figure 4:
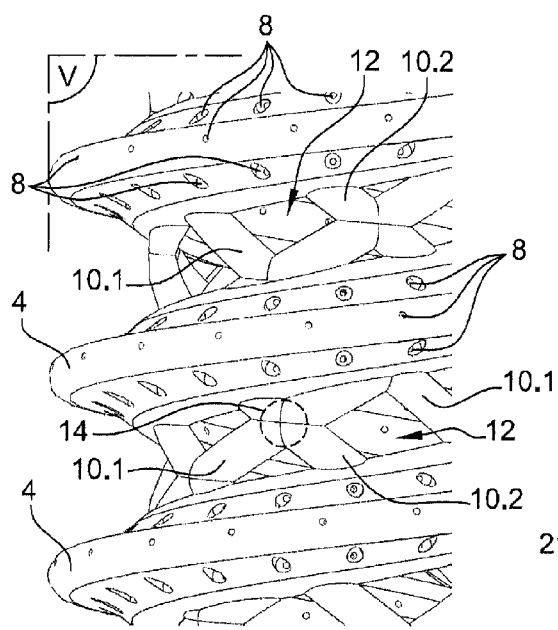
FIG. 4 is a larger scale view of a part of the intraosseous screw of FIG. 1.
Figure 5:
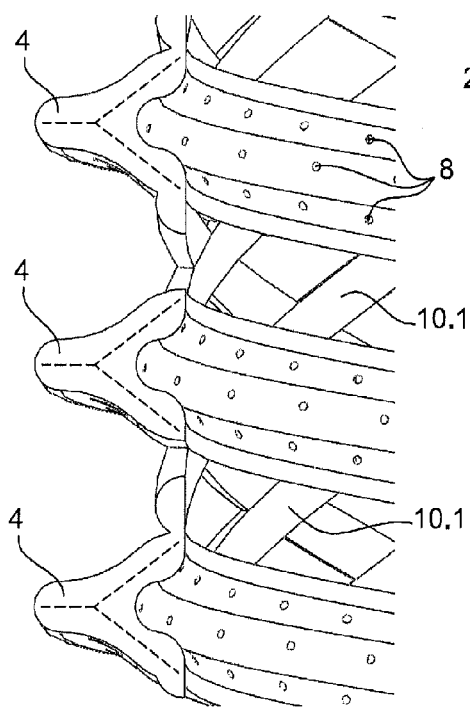
FIG. 5 is a section along a plane V in FIG. 4.

FIG. 6 illustrates an intraosseous screw 101 in accordance with a second embodiment of the invention. In as far as the intraosseous screw 101 is similar to the intraosseous screw 1, the description of the intraosseous screw 1 given herebefore in relation to FIGS. 1 to 5 can be transposed to the intraosseous screw 101, except for the noticeable differences stated below.

A component of the intraosseous screw 101 which is identical or which corresponds, by its structure or function, to a component of the intraosseous screw 1 has the same reference number increased by 100. Thus, it is defined an outer threading 102, threads 104, capillary channels 108, connecting members formed by spacers 110 and a multitude of through openings 112.

The intraosseous screw 101 differs from the intraosseous screw 1, in particular as the intraosseous screw 101 only comprises opposite spacers 110.1, whereas the intraosseous screw 101 also comprises direct spacers 110.2. Hence, the spacers 110.1 do not meet; they do not form an intersection. The through openings 114 hence have similar shapes, and generally in an incurved parallelogram shape. Thus, such an intraosseous screw 101 is relatively simple to manufacture, as it only has opposite spacers 110.1. The number and shape of the spacers 110 are selected according to the required mechanical strength, hence in particular according to the nature of the bone, for example spongy bone or cortical bone. Like the spacers 10, spacers 10 may have through capillary channels in such a manner as to open into the housing 106.

Figure 7:
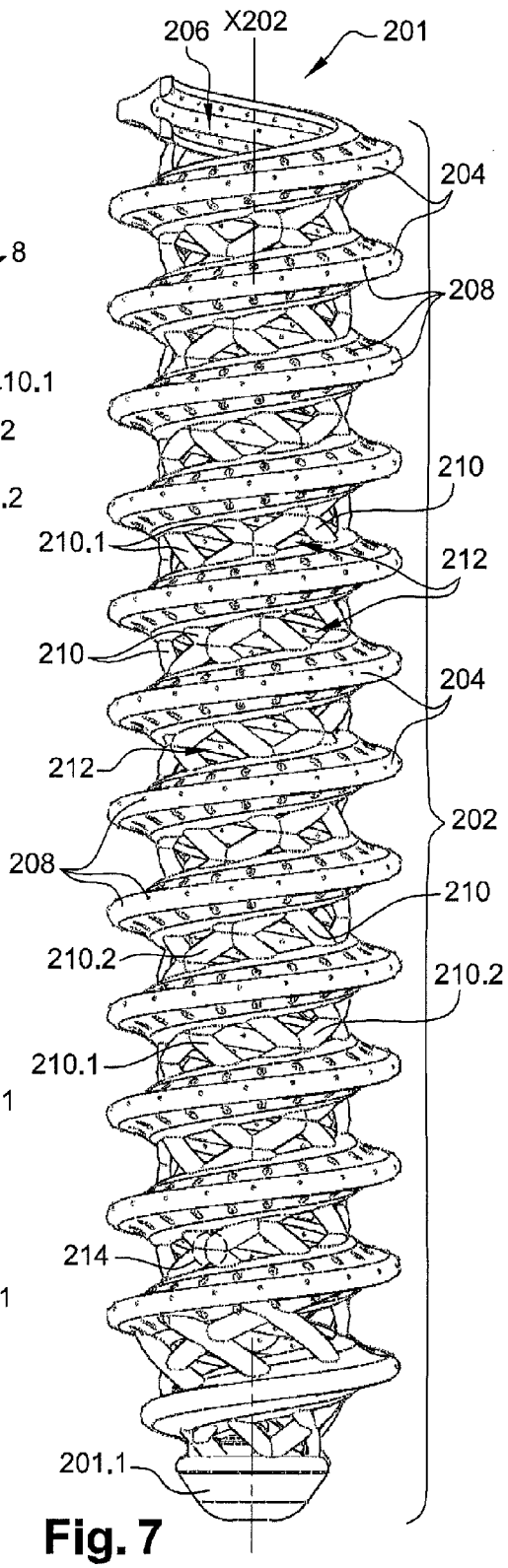
FIG. 7 is a perspective view of an intraosseous screw with a head in accordance with a third embodiment of the invention.
Figure 8:
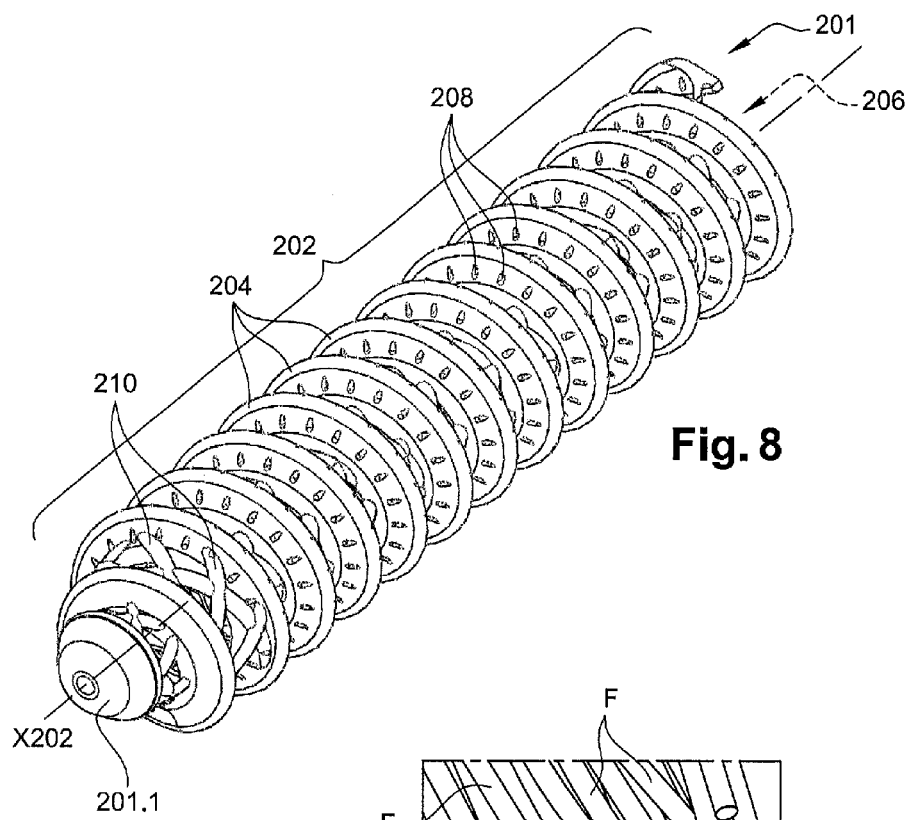
FIG. 8 is a perspective view, according to an angle different from FIG. 7, of the intraosseous screw of FIG. 7.

FIGS. 7 and 8 illustrate an intraosseous screw 201 in accordance with a third embodiment of the invention. The intraosseous screw 201 is intended for fixing a bone fragment to a bone for an osteosynthesis with a view to repairing a bone.

The intraosseous screw 201 comprises an outer threading 202 which is formed by a plurality of threads 204. The outer threading 202 extends along a so-called external helix around a longitudinal axis X202.

Contrary to the intraosseous screw 1, the intraosseous screw 201 further comprises a screw head 201.1. The screw head 201.1 is arranged in such a manner that the intraosseous screw 201 may be tightened in a bore around a portion of generally cylindrical bone, after a possible boring of the bone.

The outer threading 202 is composed of at least one biocompatible material. Each thread 204 here has a thickness of around 1 mm. The outer threading 2 here has a length of around 4 mm and an outer diameter, measured on the thread head of around 1 mm.

In addition, the intraosseous screw 201 comprises a housing 206 a part of which is visible on FIG. 7. The housing 206 extends inside the outer threading 202 and generally parallel to the longitudinal axis X202. The housing 206 delimits a hollow cylindrical volume. The hollow cylindrical volume of the housing 206 is shaped to house, after screwing the intraosseous screw 201 into the bone, a cylindrical portion of bone.

The outer threading 202 has several so-called capillary channels 208 passing through the outer threading 202 in such a manner as to open into the housing 206. In the example of FIGS. 7 and 8, the capillary channels 208 are regularly distributed over the outer threading 202. The capillary channels 208 here are distributed substantially uniformly over the outer threading 202.

The intraosseous screw 201 further comprises spacers 210, as shown in FIGS. 7 and 8. Each spacer 210 connects two consecutive threads 204. The spacers 210 here form connecting members arranged in such a manner as to connect the threads 204 together.

The spacers 210, which compose these connecting members are arranged in such a manner as to define therebetween a multitude of through openings 212 which open into the housing 206. The through openings 212 are here defined by interstices extending between spacers 210. In the example of FIGS. 7 and 8, the spacers 210 are configured in such a manner that the combined surface area of the through openings 212 represents around 60% of the surface delimited between the threads 4.

In the example of FIGS. 7 and 8, the spacers 210 comprise so-called opposite spacers 210.1 which generally extend along so-called opposite helices which are oriented inversely to the external helix of the outer threading 202. In the example of FIGS. 7 and 8, the outer threading 202 runs along an external helix which is dextral (pitch on the right). The opposite helices hence have a pitch on the left.

Spacers 210 further comprise so-called direct spacers 210.2 which extend generally along so-called direct helices which are oriented just as the external helix of the outer threading 202. The direct helices hence have a pitch on the right.

In addition, the intraosseous screw 201 has nodes 214 between two consecutive threads 204. Each node 214 is here formed by the intersection of two spacers 210, in general an opposite spacer 210.1 and a direct spacer 210.2. At least two neighboring spacers 210.1 and 210.2 meet in a node 214.

Figure 10:
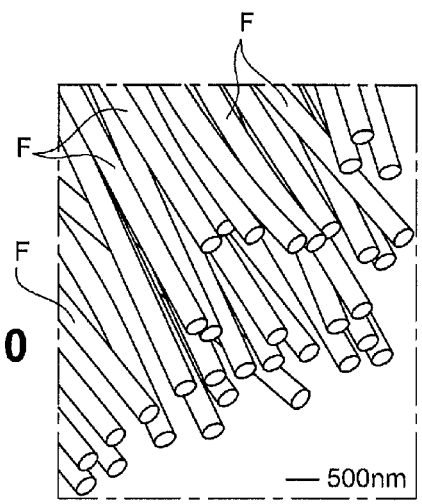
FIG. 10 is a microscopic view of a part of an intraosseous screw in accordance with the invention.

The outer threading 202 and the spacers 210, which form connecting members, are respectively composed of compressed fibers F, visible on FIG. 10. These compressed fibers here comprise fibers composed of lactic acid polymer (PLA), collagen fibers, hydroxyapatite fibers and, possibly, other resorbable fibers.

The compressed fibers further comprise strontium fibers, which make the intraosseous screw 201 radio-opaque. In addition, some of the compressed fibers are covered with spheroidal particles made of a bioactive ceramic-glass material, the spheroidal particles preferably having a dimension lower than 2 μm, preferably lower than 1 μm.

Thus, such spheres facilitate bone adhesion. Such a bioactive ceramic-glass material is commercialized for example as "bioglass" or reference BaG 13.93. The spheroidal particles may be covered with poly-L, DL lactic acid (for example known under the reference SR-PLA70).

As the capillary channels 208 and the through openings 214 are relatively wide, the blood will flow quickly therein. When composed of compressed fibers, the intraosseous screw 201 has secondary capillaries which are not represented, which extend along compressed fibers and which are narrower. The blood flows more slowly through these secondary capillaries than through the capillary channels 208 and the through openings 214. However, the blood can cross, by capillarity, a greater distance through these secondary capillaries than through the capillary channels 208 and the through openings 214.

In order to manufacture an intraosseous screw 1, 101 or 201 in accordance with the invention, a manufacturing method comprises steps of projecting fibers in a mold the cavity of which defines the intraosseous screw. This projection is carried out by electrospinning or by rotary jet spinning, under the control of a computer. A fluid is projected according to a rotary movement in such a manner as to agglomerate fibers which are oriented and positioned by means of an electrostatic field. Alternatively, the intraosseous screw 1, 101 or 201 may be manufactured along an axis by fibers projected or rotationally molded.

The invention claimed is:

1. An intraosseous screw intended for fixing a bone fragment to a bone for an osteosynthesis or a transplant for a ligament surgery, the intraosseous screw comprising:
   at least one outer threading, which is formed by a plurality of threads and which extends along an external helix around a longitudinal axis;
   a housing which extends inside the outer threading and generally parallel to the longitudinal axis; and
   connecting members arranged in such a manner as to connect the threads together;
   wherein the connecting members comprise spacers, the spacers being formed by rods and arranged in such a manner as to define a multitude of through openings which open into the housing,
   and wherein the housing delimits a hollow cylindrical volume which opens into at least one end of the outer threading, the hollow cylindrical volume being shaped in such a manner as to house, after screwing of the intraosseous screw into the bone, a cylindrical portion of bone.

2. The intraosseous screw according to claim 1, wherein transverse dimensions of the housing are greater than 90% of a minimum dimension of an inner part of the outer threading.

3. The intraosseous screw according to claim 1, wherein the hollow cylindrical volume opens at two opposed ends of the outer threading, in such a manner that, after screwing the intraosseous screw into the bone, the outer threading can house a portion of bone remaining secured to the bone.

4. The intraosseous screw according to claim 2, wherein the hollow cylindrical volume of the housing has a diameter substantially equal to an inner diameter of the at least one end of the outer threading.

5. The intraosseous screw according to claim 1, wherein the spacers intersect at least in pairs.

6. The intraosseous screw according to claim 5, wherein the spacers comprise:
   opposite spacers which generally extend along opposite helices which are oriented inversely to the external helix of said at least one outer threading; and
   direct spacers which generally extend along direct helices which are oriented like the external helix of said at least one outer threading.

7. The intraosseous screw according to claim 1, wherein said at least one outer threading has several capillary channels which cross said at least one outer threading in such a manner as to open into the housing.

8. The intraosseous screw according to claim 1, wherein at least some of the spacers have through capillary channels in such a manner as to open into the housing.

9. The intraosseous screw according to claim 7, wherein at least some elements from among said capillary channels and said through openings have shapes converging from an outer surface of the outer threading towards the housing and diverging from an outer surface of the outer threading towards the housing.

10. The intraosseous screw according to claim 1, wherein said at least one outer threading and the connecting members are respectively composed of compressed fibers.

11. The intraosseous screw according to claim 10, wherein the compressed fibers comprise fibers composed of lactic acid polymer (PLA).

12. The intraosseous screw according to claim 10, wherein the compressed fibers further comprise fibers of strontium.

13. The intraosseous screw according to claim 1, further comprising a screw head arranged in such a manner that the intraosseous screw can be tightened in a bore after previous removal of a portion of a generally cylindrical bone.

14. The intraosseous screw according to claim 1, further comprising an inner threading which extends on the edges of the housing.

15. The intraosseous screw according to claim 1, wherein each spacer extends between two consecutive threads.

16. The intraosseous screw according to claim 1, wherein the spacers are configured in such a manner that the combined surface area of the through openings represents at least 50% of the surface delimited between the threads.

17. The intraosseous screw according to claim 1, comprising at least 5 spacers, between two consecutive threads.

18. A manufacturing method, for manufacturing an intraosseous screw according to claim 1, the manufacturing method comprising steps of projecting fibers in a mold a cavity of which defines the intraosseous screw.

* * * * *